United States Patent
Bickford et al.

(10) Patent No.: US 9,827,285 B1
(45) Date of Patent: Nov. 28, 2017

(54) COMPOSITIONS AND METHODS OF IMPROVING COGNITIVE PERFORMANCE

(71) Applicants: Paula C. Bickford, Ruskin, FL (US); Cyndy Davis Sanberg, Spring Hill, FL (US); Jun Tan, Tampa, FL (US); Roland Douglas Shytle, Largo, FL (US); Paul D. Sanberg, Spring Hill, FL (US)

(72) Inventors: Paula C. Bickford, Ruskin, FL (US); Cyndy Davis Sanberg, Spring Hill, FL (US); Jun Tan, Tampa, FL (US); Roland Douglas Shytle, Largo, FL (US); Paul D. Sanberg, Spring Hill, FL (US)

(73) Assignees: University of South Florida, Tampa, FL (US); Natura Therapeutics, Inc., Tampa, FL (US); The Unites States of America as Represented by the Department of Veterans Affairs Office of General Counsel—PSG IV (024), Washington, DC (US)

( * ) Notice: Subject to any disclaimer, the term of this patent is extended or adjusted under 35 U.S.C. 154(b) by 641 days.

(21) Appl. No.: 14/291,773

(22) Filed: May 30, 2014

Related U.S. Application Data (60) Provisional application No. 61/828,987, filed on May 30, 2013.

(51) Int. Cl.

| | |
|---|---|
| *A61K 36/28* | (2006.01) |
| *A61K 36/45* | (2006.01) |
| *A61K 36/82* | (2006.01) |
| *A61K 36/87* | (2006.01) |
| *A61K 31/4172* | (2006.01) |
| *A61K 31/593* | (2006.01) |
| *A61K 31/05* | (2006.01) |

(52) U.S. Cl.
CPC ............ *A61K 36/87* (2013.01); *A61K 31/05* (2013.01); *A61K 31/4172* (2013.01); *A61K 31/593* (2013.01); *A61K 36/45* (2013.01); *A61K 36/82* (2013.01)

(58) Field of Classification Search
CPC ........ A61K 36/28; A61K 36/45; A61K 36/82; A61K 36/87
USPC ......................................... 424/729, 732, 766
See application file for complete search history.

(56) References Cited

U.S. PATENT DOCUMENTS

| | | | | |
|---|---|---|---|---|
| 4,281,061 | A * | 7/1981 | Zuk ....................... | G01N 33/542 435/188 |
| 6,572,899 | B1 * | 6/2003 | Gorsek ................ | A61K 31/122 424/725 |
| 6,602,526 | B2 * | 8/2003 | Riley ....................... | A61K 8/66 424/725 |
| 7,442,394 | B2 | 10/2008 | Davis Sanberg et al. | |
| 7,972,633 | B2 | 7/2011 | Smith | |
| 8,574,640 | B2 | 11/2013 | Davis Sanberg et al. | |
| 2009/0280199 | A1 | 11/2009 | Russell | |
| 2013/0034530 | A1 | 2/2013 | Fantz | |

FOREIGN PATENT DOCUMENTS

WO           0149307 A1        7/2001

OTHER PUBLICATIONS

Bizon JL, Lee HJ, Gallagher M. Neurogenesis in a rat model of age-related cognitive decline. Aging Cell 2004;3:227-234.
Drapeau E, Mayo W, Aurousseau C, Le Moal M, Piazza PV, Abrous DN. Spatial memory performances of aged rats in the water maze predict levels of hippocampal neurogenesis. Proc Natl Acad Sci USA 2003;100:14385-14390.
Prickaerts J, Koopmans G, Blokland A, Scheepens A. Learning and adult neurogenesis: survival with or without proliferation? Neurobiol Learn Mem 2004;81: 1-11.
Bickford PC, Gould T, Briederick L, Chadman K, Pollock A, Young D, Shukitt-Hale B, Joseph J. Antioxidant-rich diets improve cerebellar physiology and motor learning in aged rats. Brain Res 2000;866:211-217.
Bickford PC, Shukitt-Hale B, Joseph J. Effects of aging on cerebellar noradrenergic function and motor learning: nutritional interventions. Mech Ageing Dev 1999;111:141-154.
Cao G, Shukitt-Hale B, Bickford PC, Joseph JA, McEwen J, Prior RL. Hyperoxia-induced changes in antioxidant capacity and the effect of dietary antioxidants. J Appl Physiol 1999;86:1817-1822.
Tan J, Town T, Mullan M. CD45 inhibits CD40L-induced microglial activation via negative regulation of the Src/p44/42 MAPK pathway. J Biol Chem 2000; 275:37224-37231.
Chao CC, Hu S, Molitor TW, Shaskan EG, Peterson PK. Activated microglia mediate neuronal cell injury via a nitric oxide mechanism. J Immunol 1992;149:2736-2741.
Bickford, et al., Blueberry Extract Enhances Survival of Intraocular Hippocampal Transplants, Cell Transplant, 2005; 14 (4), 213-23.
Sanberg, et al., Nutraceuticals Synergistically Promote Proliferation of Human Stem Cells, Stem Cells and Dev. 2006. 118-123.
Sanberg, et al., Oxidative Stress of Neural, Hematopoietic, and stem cells: Protection by Natural Compounds, Rejuvenation Research, 2007. 173-178.
Sanberg, et al., Dietary Supplemental Exerts Neuroprotective Effects in Ischemic Stroke Model, Rejuvenation Research, 2008. 201-214.

(Continued)

*Primary Examiner* — Chris R Tate
*Assistant Examiner* — Deborah Davis
(74) *Attorney, Agent, or Firm* — Thomas|Horstemeyer, LLP (57) ABSTRACT

Provided herein are compositions, formulations, kits, and methods for improving or modifying cognitive performance in an individual having normal-age related cognitive decline. The composition can include an amount of a blueberry extract, L-carnosine, a green tea extract, vitamin $D_3$, and a grape extract. The composition can be included in a pharmaceutical formulation and be administered to a subject having normal-age related cognitive decline according to a dosing regimen.

10 Claims, 4 Drawing Sheets

(56) References Cited

OTHER PUBLICATIONS

Sanberg, et al., Acute Treatment with Herbal Extracts Provides Neuroprotective Benefits in In Vitro and in Vivo Stroke Models, Characterized by Reduced Ischemic Cell Death and Maintenance of Motor and Neurological Functions, Cell Medicine 2011. 137-142.
Mazza G. et al. J. Agric. Food Chem. (2002) 50: 7731-7737.
Manach C. et al. Am. J. Clin. Nutr. (2005) 81(suppl): 230S-42S.
Vieth R. & Fraser D. CMAJ (2002) 166: 1541-1542.
Munro I., Am. J. Clin. Nutr. (2001) 74: 865-867.
Park Y.J., Volpe S.L., Decker, E.A. J. Agric. Food Chem. (2005) 53: 4736-4739.
Cao, et al. (1995), Clin. Chem. 41:12, 1738-1744.
Acosta, S., J. Jernberg, C. D. Sanberg, P. R. Sanberg, B. J. Small, C. Gemma and P. C. Bickford (2010). "NT-020, a Natural Therapeutic Approach to Optimize Spatial Memory Performance and Increase Neural Progenitor Cell Proliferation and Decrease Inflammation in the Aged Rat." Rejuvenation. Res.
Cartford, M. C., C. Gemma and P. C. Bickford (2002). "Eighteen-Month-Old Fischer 344 Rats Fed a Spinach-Enriched Diet Show Improved Delay Classical Eyeblink Conditioning and Reduced Expression of Tumor Necrosis Factor alpha (TNFalpha) and TNFbeta in the Cerebellum." J. Neurosci. 22(14): 5813-5816.
Dai, Q., A. R. Borenstein, Y. Wu, J. C. Jackson and E. B. Larson (2006). "Fruit and vegetable juices and Alzheimer's disease: The KAME project." American Journal of Medine 119: 751-759.
Ekstrom, R. B., J. W. French, H. H. Harman and D. Dermen (1976). Manual for kit of factor referenced cognitive tests. Princeton, NJ, Educational Testing Service.
Gemma, C., M. H. Mesches, B. Sepesi, K. Choo, D. B. Holmes and P. C. Bickford (2002). "Diets enriched in foods with high antioxidant activity reverse age-induced decreases in cerebellar beta-adrenergic function and increases in proinflammatory cytokines." J.Neurosci. 22(14): 6114-6120.
Gemma, C., J. Vila, A. Bachstetter and P. C. Bickford (2007). "Oxidative stress and brain aging: From theory to prevention." 15: 353-374.
Joseph, J. A., N. Denisovan, D. Fisher, B. Shukitt-Hale, P. C. Bickford, R. Prior and G. Cao (1998). "Age-related neurodegeneration and oxidative stress: Putative Nutritional Intervention." Neurologic clinics 16(3): 747-755.
Joseph, J. A., B. Shukitt-Hale, N. A. Denisova, D. Bielinski, A. Martin, J. J. McEwen and P. C. Bickford (1999). "Reversals of age-related declines in neuronal signal transduction, cognitive, and motor behavioral deficits with blueberry, spinach, or strawberry dietary supplementation." Journal of Neuroscience 19(18): 8114-8121.
Joseph, J. A., B. Shukitt-Hale, N. A. Denisova, R. L. Prior, G. Cao, A. Martin, G. Taglialatela and P. C. Bickford (1998). "Long-term dietary strawberry, spinach, or vitamin E supplementation retards the onset of age-related neuronal signal-transduction and cognitive behavioral deficits." Journal of Neuroscience 18: 8047-8055.
Owsley, C., M. Sloane, G. McGwin and K. Ball (2002). "Timed instrumental activities of daily living tasks: Relationship to cognitive function and everyday performance assessments in older adults." Gerontology 2002: 254-265.
Rowland, I. R., H. Wiseman, T. A. Sanders, H. Adlercreutz and E. A. Bowey (2000). "Interindividual variation in metabolism of soy isoflavones and lignans: Influence of habitual diet on equol production by the gut microflora." Nutrition and Cancer 36: 27-32.
Spreen, O. and E. Strauss (1998). A compendium of neuropsychological tests: Administration, norms, and commentary. USA, Oxford University Press.
Small, et al. (2014). Neutraceutical Intervention Improves Older Adults' Cognitive Functioning, Rejuvenation Research 17:1, 27-32.
Shukitt-Hale, B. Blueberries and neuronal aging. Gerontology 2012; 58:518-523.
Devore, et al., Dietary intakes of berries and flavonoids in relation to cognitive decline. Ann Neurol 2012; 72:135-143.
Krikorian, et al., Blueberry supplementation improves memory in older adults. J Agric Food Chem 2010; 58:3996-4000.
Krikorian, et al., Concord grape juice supplementation and neurocognitive function in human aging. J. Agric Food Chem 2012; 60:5736-5742.
Salthouse, T. 2012. Annu. Rev. Psychol. 63:201-226.
Tombaugh, TN, Trail Making Test A and B: Normative data stratified by age and education, Archives of Clinical Neuropsychology 19 (2004) 203-214.
Small, et al., Tracking Cognition—Health Changes from 55 to 95 Years of Age, J Gerontology, Series B, 66B(S1), i153-i161.
Joseph, J. A., B. Shukitt-Hale, and L. M. Willis. "Grape Juice, Berries, and Walnuts Affect Brain Aging and Behavior." Journal of Nutrition 139.9 (2009): 1813S-817S.
Cories, Dietary Supplementations as Neuroprotective Therapies: Focus on NT-020 Diet Benefits in a Rat Model of Stroke, Int J. Mol Sci. 2012; 13(6) 7424-44.
Freeman, et al., Blueberry Supplementation Attenuates Microglial Activation in Hippocampal Intraocular Grafts to Aged Hosts, Glia, Apr. 15, 2010; 58(6) 679-90.
Coultrap, et al., Blueberry-Enriched Diet Ameliorates Age-Related Declines in NMDA Receptor-Dependent LTP, Age (Dordr), 2008.
Zhu, Blueberry Opposes beta-Amyloid Peptide-induced Microglial Activation Via Inhibition of P44/42 Mitogen-Activation Protein Kinase. Rejuvenation Res. Oct. 11, 2008(5), 891-901.
Willis, et al., Dietary Blueberry Supplementation Affects Growth but Not Vascularization of Neural Transplants, J. Cereb Blood Flow Metab, Jun. 2008 (6).
Yasuhara, et al., Dietary Supplementation Exerts Neuroprotective Effects in Ischemic Stroke Model, Rejuvenation Res. Feb. 2008; 11 (1).
Wang, et al., Dietary Supplementation with Blueberries, Spinach, or Spirulina Reduces Ischemic Brain Damage, Exp. Neurol, May 2005; 193.
Joseph, et al. (2003), Feeding the Aging Brain, Dana Foundation, 1-15.
Stevenson, et al. (2007), Review: Polyphenolic phytochemicals—just antioxidants or much more? Cellular and Molecular Life Sciences 64, 2900-2916.
Joseph, et al. (2005), Am J. Clin Nutr 2005:81(suppl): 313S-6S.
Willis, et al. (2009), Am J. Clin Nutr 2009:89(suppl): 1602S-6S.
Shukitt-Hale, et al. (2008), J. Agric. Food Chem. 56, 636-641.
Miller, et al. (2012), J. Agric. Food Chem. 60, 5709-5715.
Andres-Lacueva, et al. (2005), Nutritional Neuroscience 8:2, 111-120.
Malin, et al. (2011), Nutrition 27, 338-342.
Casadesus, et al. (2004), Nutritional Neuroscience 7:5/6, 309-316.
Joseph, et al. (2003), Nutritional Neuroscience 6:3, 153-162.
Elks, et al. (2011), PLoS One 6:9, 1-10.
Kaneko, et al. (2012), Int. J. Mol. Sci. 13, 7424-7444.
Willis, et al. (2005), Cell Trans 14, 213-223.
Stromberg, et al. (2005), Experimental Neurology 196, 298-307.
Bickford, et al. (2006), Stem Cells and Development 15:118-123.
Shytle, et al. (2007), Rejuvenation Research 10:2, 173-178.
Kaneko, et al. (2010), Cell Med. 1:3, 137-142.
Kaplan, et al. (2011), New York Berry Newsw 10:5, 1-28.
Perez, et al. (2015), Fruit and Tree Nuts Outlook, USDA, 1-43.
Shukitt-Hale, et al. (1998), Experimental Gerontology 33:6, 615-624.
Shukitt-Hale, et al. (1999), Age 22, 9-17.
Hauss-Wegrzyniak, et al. (2000), Brain Research 859, 157-166.
Wagster MV, King JW, Resnick SM, Rapp PR. The 87%. J Gerontol A Biol Sci Med Sci 2012;67:739-740.
Carlson MC, Erickson KI, Kramer AF, Voss MW, Bolea N, Mielke M, McGill S, Rebok GW, Seeman T, Fried LP. Evidence for neurocognitive plasticity in at-risk older adults: The Experience Corps Program. J Gerontol A Biol Sci Med Sci 2009;64A:1275-1282.
Kramer AF, Hahn S, Cohen NJ, Banich MT, McAuley E, Harrison CR, Chason J, Vakil E, Bardell L, Boileau RA, Colcombe A. Ageing, fitness and neurocognitive function. Nature 1999;400:418-419.

(56) References Cited

OTHER PUBLICATIONS

Ball KK, Berch DB, Helmers KF, Jobe JB, Leveck MD, Marsiske M, Morris JN, Rebok GW, Smith DM, Tennstedt SL, Unverzagt FW, Willis SL, for the ACTIVE Study Group. Effect of cognitive training interventions with older adults: A randomized controlled trial. JAMA 2002;288:2271-2281.

Edwards JD, Wadley VG, Myers R, Roenker DL, Cissell GM, Ball KK. Transfer of a speed of processing intervention to near and far cognitive functions. Gerontology 2002;48: 329-340.

Hertzog C, Kramer AF, Wilson RS, Lindenberger U. Enrichment effects on adult cognitive development: Can the functional capacity of older adults be preserved and enhanced? Psycholog Sci Publ Interest 2008;9:1-65.

Small BJ, Dixon RA, McArdle JJ, Grimm KJ. Do changes in lifestyle engagement moderate cognitive decline in normal aging? Evidence from the Victoria Longitudinal Study. Neuropsychology 2012;26:144-155.

Shineman DW, Salthouse TA, Launer LJ, et al. Therapeutics for cognitive aging. Ann NY Acad Sci 2010;1191(S1):1-10.

Morris MC, Evans DA, Tangney CC, Bienias JL, Wilson RS. Associations of vegetable and fruit consumption with agerelated cognitive change. Neurology 2006;67:1370-1376.

Craft S, Foster TC, Landfield PW, Maier SF, Resnick SM, Yaffe K. Session III: Mechanisms of age-related cognitive change and targets for intervention: Inflammatory, oxidative, and metabolic processes. J Gerontol A Biol Sci Med Sci 2012;67:754-759.

Milgram NW, Head E, Zicker SC, Ikeda-Douglas CJ, Murphey H, Muggenburg B, Siwak C, Tapp D, Cotman CW. Learning ability in aged beagle dogs is preserved by behavioral enrichment and dietary fortification: A two-year longitudinal study. Neurobiol Aging 2005;26:77-90.

Head E, Murphey HL, Dowling AL, McCarty KL, Bethel SR, Nitz JA, Pleiss M, Vanrooyen J, Grossheim M, Smiley JR, Murphy MP, Beckett TL, Pagani D, Bresch F, Hendrix C. A combination cocktail improves spatial attention in a canine model of human aging and Alzheimer's disease. J Alzheimers Dis 2012;32:1029-1042.

Folstein M, Folstein S, McHugh P. "Mini-mental state": A practical method for grading the cognitive state of patients for the clinician. J Psychiatr Res 1975;12:189-198.

Ware JE, Kosinsiki M, Keller SD. A 12-item short-form health survey: Construction of scales and preliminary tests of reliability and validity. Med Care 1996;34:220-233.

Radloff LS. The CES-D scale: A self-report depression scale for research in the general population. Appl Psycholog Measurement 1977;1:385-401.

Lindenberger U, Mayr U, Kliegl R. Speed and intelligence in old age. Psychol Aging 1993;8:207-220.

Salthouse TA. The processing speed theory of adult age differences in cognition. Psycholog Rev 1996;103:403-428.

Chapman SB, Cotman CW, Fillit HM, Gallagher M, van Dyck CH. Clinical trials: New opportunities. J Gerontol A Biol Sci Med Sci 2012;67:773-780.

Ogawa M. (1993). Differentiation and proliferation of hematopoietic stem cells. Blood 81:2844-2853.

Socolovsky M, SN Constantinescu, S Bergelson, A Sirotkin and HF Lodish. (1998). Cytokines in hematopoiesis: specificity and redundancy in receptor function. Adv Protein Chem 52:141-198.

Whetton AD and E Spooncer. (1998). Role of cytokines and extracellular matrix in the regulation of haemopoietic stem cels. Curr Opin Cell Biol 10:721-726.

Henschler R, W Brugger, T Luft, T Frey, R Mertelsmann and L Kanz. (1994). Maintenance of transplantation potential in ex vivo expanded CD34()-selected human peripheral blood progenitor cells. Blood 84:2898-2903.

Miller CL and CJ Eaves. (1997). Expansion in vitro of adult murine hematopoietic stem cells with transplantable lympho- myeloid reconstituting ability. Proc Natl Acad Sci USA 94:13648-13651.

Demetri GD and JD Griffin. (1991). Granulocyte colony-stimulating factor and its receptor. Blood 78:2791-2808.

Adamson JW and JW Eschbach. (1990). Treatment of the anemia of chronic renal failure with recombinant human erythropoietin. Annu Rev Med 41:349-360.

Eschbach JW (1989). The anemia of chronic renal failure: pathophysiology and effects of recombinant erythropoietin. Kidney International 35, 134-148.

Koury MJ and P Ponka. (2004). New insights into erythropoiesis: the roles of folate, vitamin B12, and iron. Annu Rev Nutr 24:105-131.

Hisha H, H Yamada, MH Sakurai, H Kiyohara, Y Li, C Yu, N Takemoto, H Kawamura, K Yamaura, S Shinohara, Y Komatsu, M Aburada and S Ikehara. (1997). Isolation and identification of hematopoietic stem cell-stimulating substances from Kampo (Japanese herbal) medicine, Juzentaiho-to. Blood 90:1022-1030.

Hisha H, U Kohdera, M Hirayama, H Yamada, T Iguchi-Uehira, TX Fan, YZ Cui, GX Yang, Y Li, K Sugiura, M Inaba, Y Kobayashi and S Ikehara. (2002). Treatment of Shwachman syndrome by Japanese herbal medicine (Juzen-taiho-to): stimulatory effects of its fatty acids on hemopoiesis in patients. Stem Cells 20:311-319.

Holehouse EL, ML Liu and GW Aponte. (1998). Oleic acid distribution in small intestinal epithelial cells expressing intestinal-fatty acid binding protein. Biochim Biophys Acta 1390:52-64.

Meyer C. (2004). Scientists probe role of vitamin D: deficiency a significant problem, experts say. J Am Med Assn 292:1416-1418.

Mathieu C, EE van, B Decallonne, A Guilietti, C Gysemans, R Bouillon and L Overbergh. (2004). Vitamin D and 1,25-dihydroxyvitamin D3 as modulators in the immune system. J Steroid Biochem Mol Biol 89-90:449-452.

Hipkiss AR, JE Preston, DT Himsworth, VC Worthington, M Keown, J Michaelis, J Lawrence, A Mateen, L Allende, PA Eagles and NJ Abbott. (1998). Pluripotent protective effects of carnosine, a naturally occurring dipeptide. Ann NY Acad Sci 854:37-53.

Holliday R and GA McFarland. (2000). A role for carnosine in cellular maintenance. Biochemistry (Mosc.) 65: 843-848.

Williams RJ, JP Spencer and C Rice-Evans. (2004). Flavonoids: antioxidants or signalling molecules? Free Radic Biol Med 36:838-849.

Chen ZP, JB Schell, CT Ho and KY Chen. (1998). Green tea epigallocatechin gallate shows a pronounced growth inhibitory effect on cancerous cells but not on their normal counterparts. Cancer Lett 129:173-179.

Wang YC and U Bachrach. (2002). The specific anti-cancer activity of green tea ()-epigallocatechin-3-gallate (EGCG). Amino Acids 22:131-143.

Song DU, YD Jung, KO Chay, MA Chung, KH Lee, SY Yang, BA Shin and BW Ahn. (2002). Effect of drinking green tea on age-associated accumulation of Maillard-type fluorescence and carbonyl groups in rat aortic and skin collagen. Arch Biochem Biophys 397:424-429.

Bomser J, DL Madhavi, K Singletary and MA Smith. (1996). In vitro anticancer activity of fruit extracts from Vaccinium species. Planta Med 62:212-216.

McFarland G and R Holliday. (1999). Differential response of embryonic stem cells and teratocarcinoma cells to carnosine. In Vitro Cell Dev Biol Anim 35:15-16.

Hussain EA, RR Mehta, R Ray, TK Das Gupta and RG Mehta. (2003). Efficacy and mechanism of action of 1alpha-hydroxy-24-ethyl-cholecalciferol (1alpha[OH]D5) in breast cancer prevention and therapy. Recent Results Cancer Res 164:393-411.

English D. The hope and hype of nonembryonic stem cells. J Hematother Stem Cell Res 2003;12:253-254.

Semba RD, Margolick JB, Leng S, Walston J, Ricks MO, Fried LP. T cell subsets and mortality in older community-dwelling women. Exp Gerontol 2005;40: 81-87.

Ito K, Hirao A, Arai F, Takubo K, Matsuoka S, Miyamoto K, Ohmura M, Naka K, Hosokawa K, Ikeda Y, Suda T. Reactive oxygen species act through p38 MAPK to limit the lifespan of hematopoietic stem cells. Nat Med 2006;12:446-451.

Conboy IM, Conboy MJ, Wagers AJ, Girma ER, Weissman IL, Rando TA. Rejuvenation of aged progenitor cells by exposure to a young systemic environment. Nature 2005;433:760-764.

Dimmeler S, Vasa-Nicotera M. Aging of progenitor cells: limitation for regenerative capacity? J Am Coll Cardiol 2003;42:2081-2082.

(56) References Cited

OTHER PUBLICATIONS

Kuhn HG, Dickinson-Anson H, Gage FH. Neurogenesis in the dentate gyms of the adult rat: age-related decrease of neuronal progenitor proliferation. J Neurosci 1 1996;16:2027-2033.

Hill JM, Zalos G, Halcox JP, Schenke WH, Waclawiw MA, Quyyumi AA, Finkel T. Circulating endothelial progenitor cells, vascular function, and cardiovascular risk. N Engl J Med 2003;348:593-600.

Vasa M, Fichtlscherer S, Aicher A, Adler K, Urbich C, Martin H, Zeiher AM, Dimmeler S. Number and migratory activity of circulating endothelial progenitor cells inversely correlate with risk factors for coronary artery disease. Circ Res 2001;89E1-7.

* cited by examiner

COMPOSITIONS AND METHODS OF IMPROVING COGNITIVE PERFORMANCE

CROSS-REFERENCE TO RELATED APPLICATIONS

This application claims the benefit of U.S. provisional patent application No. 61/828,987 filed on May 30, 2013, the disclosure of which is incorporated herein in its entirety.

BACKGROUND

Approximately 87 percent of the population of the United States will experience some degree of cognitive decline as a consequence of the normal aging process. Normal age-related cognitive decline typically begins at about age 25. Cognitive changes that are typically observed include a reduced numerical/arithmetic ability and the speed at which one processes information. From an individual's late thirties or forties to as late as the individual's 50's or 60's, episodic or declarative memory function typically decreases. Word knowledge, vocabulary, and word reading typically remain stable into late adulthood (age 70 and greater). Typically an individual's attention span decreases with age as well.

Normal age-related cognitive decline is a complex process and is likely related to a deterioration of the various biological systems that underlie cognitive ability (i.e., the ability to think and reason). Age-related insults such as chronic inflammation, oxidative stress, insulin resistance, endothelial dysfunction, and declining hormone levels, are believed to play roles in the physical deterioration of the brain and subsequent age-related decline in cognitive ability. In short, age-related neuroanatomical and biological changes are believed to play a role in the variance in cognitive ability between young and aged individuals.

Normal age-related decline in cognitive ability is implicated in the general decrease in intellectual achievements across a variety of technical fields, including research activities, number of inventions, number of published articles or other creative works such as paintings, and overall production of high-quality products (e.g. highly-cited articles or discoveries recognized as the basis for a Nobel Prize). See e.g. Salthouse, T. 2012. Annu. Rev. Psychol. 63:201-226. The decline in cognitive ability related to the normal aging process has also been implicated in an age-related reduction in job performance. Moreover, the age-related neuro physical deterioration may affect mood, sleep patterns, and overall quality of life.

Given the prevalence and negative consequences of normal age-related cognitive decline, there exists a long-felt need for preventing or delaying the onset of normal age-related cognitive decline and improving the cognitive performance in an individual suffering from normal age-related cognitive decline.

SUMMARY

Briefly described, embodiments of the present disclosure provide compositions, formulations, kits, and methods for improving, treating, and/or preventing cognitive decline, particularly normal age-related cognitive decline. The present disclosure provides for compositions containing an amount of a blueberry extract, an amount of L-carnosine, an amount of a green tea extract, an amount of vitamin $D_3$, and an amount of a grape extract.

In some embodiments, the compositions contain about 350 mg to about 25 g of blueberry extract, about 10 mg to about 200 mg of L-carnosine, about 350 mg to about 25 mg of green tea extract, 50 IU to about 4000 IU of vitamin $D_3$, and about 1 mg to about 60 mg of grape extract. In some embodiments, the composition contains 350 mg to about 25 g of blueberry extract, about 10 mg to about 200 mg of L-carnosine, about 350 mg to about 25 mg of green tea extract, 200 IU of vitamin $D_3$, and about 1 mg to about 60 mg of grape extract.

For some embodiments, the grape extract is a full spectrum grape extract. In other embodiments, the composition contains about 5 percent to about 20 percent (w/w) epigallocatechin gallate (EGCG). In further embodiments, the composition contains about 25 percent to about 75 percent (w/w) polyphenolic compounds. In some embodiments, the composition contains about 0.20 to about 0.70 percent (w/w) resveratrol. In further embodiments, the composition contains a pharmaceutically acceptable carrier or excipient.

Also provided are methods of administering to a subject a dosage form containing an amount of blueberry extract, an amount of L-carnosine, an amount of green tea extract, an amount of vitamin D3, and an amount of a grape extract. In some embodiments, the dosage form administered contains a composition having about 350 mg to about 25 g of blueberry extract, about 10 mg to about 200 mg of L-carnosine, about 350 mg to about 25 mg of green tea extract, 50 IU to about 4000 IU of vitamin $D_3$, and about 1 mg to about 60 mg of grape extract. In some embodiments, the grape extract within the administered dosage form is a full spectrum grape extract. In further embodiments, the administered dosage form contains a pharmaceutical carrier or excipient.

In some embodiments the dosage form is administered once daily. In other embodiments, the dosage form is administered twice daily. For some embodiments, the dosage form is selected from the group consisting of a tablet, capsule, soft gel, gel cap, liquid, paste, spray, or powder. In some embodiments, the dosage form is administered orally. In other embodiments, administration of the dosage form occurs daily for 2 days to about 1 year.

For some embodiments, the dosage form containing an amount of blueberry extract, an amount of L-carnosine, an amount of green tea extract, an amount of vitamin D3, and an amount of a grape extract is administered to a subject having normal age-related cognitive decline. In further embodiments, administration of the dosage form containing an amount of blueberry extract, an amount of L-carnosine, an amount of green tea extract, an amount of vitamin D3, and an amount of a grape extract improves cognitive performance as measured by a cognitive performance assessment test.

Also described herein are kits containing a dietary supplement formulation containing about 350 mg to about 25 g of blueberry extract, about 10 mg to about 200 mg of L-carnosine, about 350 mg to about 25 g of a green tea extract, about 50 IU to about 4000 IU of vitamin D3, about 1 mg to about 60 mg of a full spectrum grape extract, and a pharmaceutically acceptable carrier, and instructions that are present in a tangible medium of expression and indicate that the dietary supplement formulation is for use in a subject having normal age-related cognitive decline.

DETAILED DESCRIPTION

Definitions

In describing the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within .+−.10% of the indicated value, whichever is greater.

As used herein, "active derivative" and the like refers to a modified composition containing blueberry extract, L-carnosine, green tea extract, vitamin $D_3$, and grape extract that retains an ability to improve the cognitive performance in a subject. Assays for testing the ability of an active derivative to perform in this fashion are known to those of ordinary skill in the art.

As used herein, "control" is an alternative subject or sample used in an experiment for comparison purposes and included to minimize or distinguish the effect of variables other than an independent variable.

As used herein, "drug product," "pharmaceutical dosage form," "dosage form," "final dosage form" and the like, refer to a pharmaceutical formulation that is administered to a subject in need of treatment and generally may be in the form of tablets, capsules, sachets containing powder or granules, liquid solutions or suspensions, patches, and the like. The terms also encompass dosage forms of compounds that are considered nutraceuticals or dietary supplements.

As used herein, "effective amount" is an amount sufficient to effect beneficial or desired results. An effective amount can be administered in one or more administrations, applications, or dosages.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "cognitive performance" and "cognitive ability" refer to near-transfer cognitive abilities and/or far-transfer cognitive abilities. Near-transfer cognitive abilities include, but are not limited to, cognitive speed of processing, reaction time, and executive functioning. Far-transfer cognitive abilities include, but are not limited to, memory and visual-spatial ability.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo. Pharmaceutical formulation as used herein also includes the term "nutraceutical formulation."

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. These terms also encompass compounds that are nutraceutically acceptable carriers for excipients.

As used herein, "pharmaceutically acceptable salt" refers to any acid or base addition salt whose counter-ions are non-toxic to the subject to which they are administered in pharmaceutical doses of the salts.

As used herein, "nutraceutically effective amount," "pharmaceutically effective amount," "therapeutically effective amount," or "therapeutically effective dose" refer to the amount of a compound that will elicit the biological or medical response of a tissue, system, animal, or human that is being sought by the researcher, veterinarian, medical doctor or other clinician. The nutraceutically, pharmaceutically, or therapeutically, effective amount or dose will vary depending on the compound, the disorder or condition (normal or abnormal) and its severity, the route of administration, time of administration, rate of excretion, drug or nutraceutcical combination, judgment of the researcher, veterinarian, medical doctor or other clinician, dosage form, and the age, weight, general health, sex and/or diet of the subject to be treated.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "therapeutic" refers to treating or curing a disease or condition.

As used herein, "preventative" refers to hindering or stopping a disease or condition before it occurs or while the disease or condition is still in the sub-clinical phase.

As used herein, "separated" refers to the state of being physically divided from the original source or population such that the separated compound, agent, particle, chemical compound, or molecule can no longer be considered part of the original source or population.

As used herein, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data in stored on a suitable device such as a flash memory or CD-ROM.

As used herein, "normal age-related cognitive decline" refers to the reduction in cognitive performance that is associated with the normal aging process as opposed to the reduction in cognitive ability that is associated with a known disease or disorder or that is the result of an injury. See e.g. Hofer, S. M., & Alwin, D. F. (Eds.). (2008). Handbook of cognitive aging: Interdisciplinary perspectives. Los Angeles, Calif.: Sage; Dixon, R. A., Small, B. J., MacDonald, S. W. S., & McArdle, J. J. (2012). Yes, memory declines with aging—but when, how, and why? In M. Naveh-Benjamin & N. Ohta (Eds.), Memory and aging: Current issues and future directions (pp. 325-347). New York, N.Y.: Psychology Press; and Small, B. J., et. al. (2011). J. Gerontol. B. Psychol. Sci. Soc Sci. 66 (suppl 1), 153-161.

As used herein, "mild cognitive impairment" refers to a disease or disorder that causes a slight but noticeable and measureable decline in cognitive abilities, including memory and thinking skills. The changes in cognitive abilities of a subject suffering from mild cognitive impairment are more severe diagnostically compared to the cognitive impairment of an age matched subject suffering from normal age-related cognitive decline, but less severe diagnostically compared to a subject having dementia, Alzheimer's disease, or Parkinson's disease. Mild cognitive impairment is often a precursor to a more severe disease or disorder such as dementia, Alzheimer's disease, or Parkinson's disease.

As used herein, "abnormal cognitive decline" refers to a reduction in cognitive performance that is associated with or the direct result of a disease, disorder, or injury. This is in contrast to the cognitive decline that is associated with the normal aging process.

As used herein, "dementia" is the loss of cognitive abilities such as thinking, memory, and reasoning that is severe enough to interfere with a person's daily functioning. It is a disorder that is characterized by its symptoms, particularly the loss of cognitive abilities, which are the result of underlying diseases or conditions.

As used herein, "dietary supplement" refers to a product that is taken by mouth (orally) that contains a "dietary ingredient" intended to supplement the diet. Dietary supplements can also be or include extracts or concentrates, and may be found in any suitable form such as tablets, capsules, soft gels, gel caps, liquids or powders.

As used herein, "dietary ingredient" refers to products typically found in the diet and may include the following: vitamins, minerals, herbs or other botanicals, amino acids, and substances such as enzymes, organ tissues, glandular, and metabolites.

As used herein, "nutraceutical" refers to a dietary supplement that provides health benefits in addition to its basic nutritional value.

As used herein, "polyphenol" or "polyphenolic compound" refers to the class of organic chemicals characterized by the presence of large multiples of phenol structural units. There are over 4,000 distinct polyphenol species.

As used herein, "antioxidant" refers to a molecule or compound that inhibits the oxidation of other molecules or compounds.

As used herein, "synergistic effect," "synergism," or "synergy" refers to an effect arising between two or more molecules, compounds, substances, factors, or compositions that produces an effect that is greater than or different from the sum of their individual effects.

As used herein, "additive effect" refers to an effect arising between two or more molecules, compounds, substances, factors, or compositions that produces an effect that is equal to or the same as the sum of their individual effects.

As used herein, "extract" refers to a fraction or component of a plant or plant part that is withdrawn or removed from the plant or plant part by a physical or chemical process.

As used herein, "green tea extract" refers to an extract produced from part or all of a green tea plant or bush, including but not limited to *Camellia sinesis*.

As used herein, "blueberry extract" refers to an extract produced from part or all of a blueberry plant, including all or part of the fruit, of the section Cyanococcus *Vaccinium*, including but not limited to *vaccinium alaskaense, vaccinium angustifolium, vaccinium boreale, vaccinium caesariense, vaccinium corymbosum, vaccinium constablaei, vaccinium darrowii, vaccinium elliottii, vaccinium formosum, vaccinium fuscatum, vaccinium hirsutum, vaccinium myrsinites, vaccinium myrtillus, vaccinium operium, vaccinium pallidum, vaccinium simulatum, vaccinium tenellum,* and *vaccinium virgatum*.

As used herein, "grape extract" refers to an extract produced from part or all of a grape plant, including all or part of the fruit, of the genus *Vitis*, including but not limited to *Vitis vinifera, Vitis carignane, Vitis cinsault, Vitis labrusca, Vitis riparia, Vitis rotundifolia,* and *Vitis amurensis*.

As used herein, "full spectrum grape extract" refers to a grape extract that includes all parts of the grape including the seeds, skin, and pulp of the fruit.

Discussion

As discussed above, interventions to maintain and/or improve the cognitive health of an individual suffering from normal age-related cognitive decline is of critical importance. There has been interest in interventions to lessen normative age-related declines in functioning, including those directed at physical activity, gains through cognitive training efforts, as well as changes in the extent to which older adults are cognitively stimulated throughout their lives. Some efforts have been made to explore the potential role of dietary supplements, nutraceuticals, and other therapeutics in the cognitive performance of older adults.

Oxidative stress increases during the normal aging process and is implicated in the etiology of normal age-related cognitive decline. The brain is particularly susceptible to oxidative damage as it consumes roughly 20 percent of the oxygen used by the entire body and contains high concentrations of phospholipids, which are prone to oxidative damage in the context of a high metabolic rate. A result of the normal aging process is an increase in the amount of DNA and lipids within the brain that have oxidative damage. As normal aging occurs, this free radical damage leads to neuron death. Oxidative stress has also been implicated in the pathology of mild cognitive impairment and other age-related cognitive abnormalities and neurodegenerative diseases, such as Alzheimer's disease.

Polyphenols have been extensively studied for their ability to function as anti-oxidants. Polyphenolic compounds are one class of phytochemicals of which over 4000 different structures have been identified. These polyphenolic compounds occur ubiquitously in foods of plant origin. Polyphenols are the most abundant anti-oxidants in a balanced diet. The benefits of polyphenols derived from fruit and vegetable juices for the cognitive health of older adults suffering from Alzheimer's disease, a neurodegenerative disorder, have been observed. See e.g. Dai, Q., et al. 2006. Am. J. Med. 449:751-759. Others have investigated the potential effects of blueberries and strawberries on age-related changes in neuronal aging and rate of cognitive decline in animals. See e.g. Shukitt-Hale, B. 2012. Gerontology 58:518-523 and Devore E. E., et al. 2012. Ann. Neurol. 72:135-143. Although the potential antioxidant effects of polyphenolic compounds have been documented, it is limited at least by the nonuse of correlational data, lack of assessment of the bioavailability of polyphenolic compounds from diets, effect of interactions with other compounds, effect of administration route and regimen, and/or effect in humans not having a neurodegenerative disorder or a known predisposition to a neurodegenerative disorder.

Provided herein are compositions, formulations, and methods for preventing or delaying the onset of normal age-related cognitive decline and/or improving the cognitive performance in an individual suffering from normal age-related cognitive decline. Normal age-related cognitive decline is cognitive decline that is not associated with any currently known or characterized age-related disease or disorder, which has symptoms of decreased cognitive ability or performance. Instead, this normal age-related cognitive decline is the reduction in cognitive ability and performance that is associated with the normal aging process.

In some embodiments, the compositions, formulations, and methods are also useful for treating, preventing, or mitigating the symptoms, particularly the decline in cognitive performance, of an age-related cognitive disease or disorder. Cognitive decline associated with an age-related cognitive disease or disorder is referred to herein as abnormal cognitive decline. Generally, in an embodiment the composition contains blueberry extract, L-carnosine, green tea extract, vitamin $D_3$, and grape extract. The compositions provided herein can be used to treat, prevent, or mitigate symptoms associated with normal age-related cognitive decline to improve cognitive performance in a patient in need thereof.

Compositions

In some embodiments the compositions disclosed herein contain amounts of a blueberry extract, L-carnosine, green tea extract and vitamin D3. In further embodiments, the compositions also contain an amount of a grape extract. In some embodiments, the composition contains about 350 mg to about 25 g of a blueberry extract, about 10 mg to about 100 mg of L-carnosine, about 350 mg to about 25 g of green tea extract, and about 50 IU to about 4000 IU of vitamin $D_3$.

The compositions described herein contain polyphenolic compounds that are derived from the various components that make up the composition. Flavonoids are a subset of these polyphenolic compounds and include, but are not limited to, flavones, flavonols, flavanones, flavanols and their polymers, Isoflavone phytoestrogens, stilbenoids, and anthocyanins. The compositions described herein can contain one or more of these flavonioids. The flavonoids contained within the composition can be derived from any of the components contained within the composition apart from L-carnosine and vitamin $D_3$. For example, in some embodiments, the blueberry extract is a source of anthocyanins. In other embodiments, the green tea extract is a source of flavonols (e.g. catechin, epicatechin, and epigallocatechin gallate (EGCG)). In further embodiments, the grape extract is a source of stillbenoids (e.g. resveratrol). As such, the composition can also be characterized based on its content of these various phenolic compounds.

In some embodiments, the total amount of polyphenolic compounds in the composition ranges from about 25 percent to about 75 percent (w/w) of the total composition. In an embodiment, the total amount of polyphenolic compounds in the composition ranges from about 25 to about 75 percent (w/w) of the total composition. In another embodiment, the total amount of polyphenolic compounds in the composition is about 50 percent (w/w) of the total composition. The polyphenolic compounds can come from any suitable component of the composition or a combination of components of the composition.

In some embodiments, the total amount of EGCG in the composition ranges from about 5 percent to about 20 percent (w/w) of the total composition. In an embodiment, the total amount of EGCG in the composition ranges from about 5 to about 20 percent (w/w) of the total composition. In another embodiment, the total amount of EGCG in the composition is about 19 percent (w/w) of the total composition. The EGCG can come from any suitable component of the composition or a combination of components of the composition. In some embodiments, the EGCG is at least partly derived from the green tea extract.

In some embodiments, the total amount of resveratrol in the composition ranges from about 0.20 percent to about 0.70 percent (w/w) of the total composition. In an embodiment, the total amount of resveratrol in the composition ranges from about 0.29 to about 0.68 percent (w/w) of the total composition. In another embodiment, the total amount of resveratrol in the composition is about 0.68 percent (w/w) of the total composition. The resveratrol can come from any suitable component of the composition or a combination of components of the composition. In some embodiments, the resveratrol is at least partly derived from the grape extract.

In further embodiments, the total amount of anthocyanins in the composition ranges from about 1 percent to about 25 percent (w/w) of the total composition. In an embodiment, the total amount of anthocyanins in the composition ranges from about 2 to about 20 percent (w/w) of the total composition. In another embodiment, the total amount of anthocyanins in the composition is about 2.38 percent (w/w) of the total composition. The anthocyanins can come from any suitable component of the composition or a combination of components of the composition. In some embodiments, the anthocyanins are derived at least in part from the blueberry extract. In other embodiments, the anthocyanins are derived at least in part from the green tea extract.

As previously discussed, blueberries contain phytochemicals, including polyphenols, which are antioxidants. In some embodiments, the composition contains between about 350 mg to about 25 g of blueberry extract. The blueberry extract can be obtained from any suitable source and can be freeze dried, fresh, solid or liquid.

For some embodiments, the total amount of polyphenolic compounds in the blueberry extract is at least 3 percent (w/w) of the blueberry extract. In an embodiment, the total amount of polyphenolic compounds in the blueberry extract ranges from about 3 to about 35 percent (w/w) of the blueberry extract. In another embodiment, the total amount of phenolic compounds in the blueberry extract ranges from about 3 to about 30 percent (w/w) of the blueberry extract. In an embodiment, the total amount of polyphenolic compounds in the blueberry extract is about 30 percent (w/w) of the blueberry extract.

In further embodiments, the amount of anthocyanins in the blueberry extract is at least 12 percent (w/w) of the blueberry extract. In an embodiment, the total amount of anthocyanins in the blueberry extract ranges from about 1 to about 15 percent (w/w) of the blueberry extract. In another embodiment, the total amount of anthocyanins in the blueberry extract ranges from 2 to about 12 percent (w/w) of the blueberry extract. In an embodiment, the total amount anthocyanins in the blueberry extract is about 12 percent (w/w) of the blueberry extract.

In some embodiments, the amount of blueberry extract present in the final composition is based on achieving a desired amount of a compound contained in the blueberry extract in the final composition. In some of these embodiments, the amount of green tea extract used is dependent upon the amount of a particular compound present in the green tea extract used in the composition.

In some embodiments, the amount of polyphenolic compounds derived from the blueberry extract in the composition ranges from about 1 to about 35 percent (w/w) of the final composition. In further embodiments, the amount of polyphenolic compounds derived from the blueberry extract in the composition ranges from about 3 to about 30 percent (w/w) of the final composition. In an embodiment, the amount of polyphenolic compounds derived from the blueberry extract in the composition is about 30.

In some embodiments, the composition contains L-carnosine. L-carnosine is a dipeptide containing the amino acids alanine and histidine. The exact function of L-carnosine in humans and animals remains unknown, however it is thought to have antioxidant properties. The role of L-carnosine in neurodegenerative disorders, such as Parkinson's, Alzheimer's, and other dementia disorders has been evaluated, but yet remains to be understood. The role of L-carnosine, in the normal age-related cognitive decline has yet to be investigated. For some embodiments, the amount of L-carnosine in the composition is between about 10 mg and about 200 mg. In an embodiment, the composition contains about 100 mg of L-carnosine.

Tea is a drink from made from the leaves of a tea plant. Tea leaves contain many phytochemicals, some of which are antioxidants. Some of the phytochemicals found in tea leaves include caffeine, boheic acid, theobromine, aspalathin, nothofagin, gallic acid, and polyphenolic compounds, which includes the flavonoids. Some of the flavonids found in tea leaves include, but are not limited to, catechins, epicatechins, which includes epigallocatechin gallate (EGCG), tannins, and anthocyanins. Different types of teas have different phytochemical profiles due in part to the different processing methods used to prepare the teas from the leaves and the age of the leaves used. Teas are generally grouped into black, green, red (rooibos), oolong, and white tea. The grouping relates to the type of plant, the age of the leaves that are used to make the teas and the amount of processing done to obtain the tea leaves. Black, green, oolong, and white teas are made from leaves of tea plant (*Camellia sinesis*). Red tea is produced from leaves of the rooibos plant (*Aspalathus linearis*). Green tea is rich in many of these phytochemicals including the polyphenolic compounds EGCG and anthocyanins.

In some embodiments, the composition contains an amount of a green tea extract. In some embodiments, the composition contains about 350 mg to 25 g of green tea extract. In some embodiments, the green tea extract is selected from the group consisting of green tea extract, white green tea extract, red green tea extract, black green tea extract, or combinations thereof. In an embodiment, the composition contains an amount of green tea extract.

In further embodiments, the green tea extract is standardized to the amount of total polyphenolic compounds present in the green tea extract. In an embodiment, the total amount of total polyphenolic compounds in the green tea extract ranges from about 70 to about 98 percent (w/w) of the green tea extract. In another embodiment, the total amount of total polyphenolic compounds in the green tea extract ranges from about 75 to about 95 percent (w/w) of the green tea extract. In an embodiment, the total amount total polyphenolic compounds in the green tea extract is about 95 percent (w/w) of the green tea extract.

In other embodiments, the green tea extract is standardized to the amount of EGCG present in the green tea extract. In an embodiment, the total amount of EGCG in the green tea extract ranges from about 30 to about 50 percent (w/w) of the green tea extract. In another embodiment, the total amount of EGCG in the green tea extract ranges from about 30 to about 45 percent (w/w) of the green tea extract. In an embodiment, the total amount EGCG in the green tea extract is about 45 percent (w/w) of the green tea extract.

In some embodiments, the amount of green tea extract present in the final composition is based on achieving a desired amount of a compound contained in the green tea extract in the final composition. In some of these embodiments, the amount of green tea extract used is dependent upon the amount of a particular compound present in the green tea extract used in the composition. In some embodiments, the amount of polyphenolic compounds in the final composition derived from the green tea extract ranges from about 30 to about 50 percent (w/w) of the final composition. In an embodiment, the amount of polyphenolic compounds derived from the green tea extract in the composition is 40 percent (w/w) of the final composition. In some embodiments, the amount of EGCG in the final composition derived from the green tea extract ranges from about 10 to about 20 percent (w/w) of the final composition. In an embodiment, the amount of EGCG derived from the green tea extract in the composition is about 19 percent (w/w) of the final composition In further embodiments, the composition contains vitamin $D_3$ (cholecalciferol). The amount of vitamin $D_3$ in the composition can range between about 50 IU to about 4000 IU. In an embodiment, the composition contains about 200 IU of vitamin $D_3$. Vitamin $D_3$ can be obtained from any suitable source and can be derived directly from natural sources or synthetically produced from, for example, the vitamin $D_3$ precursor cholesterol.

Grapes contain many phytochemicals, including polyphenolic compounds such as, proanthocyanidins and resveratrol. In some embodiments, the composition contains a grape extract. In an embodiment, the grape extract is a full spectrum grape extract. The grape extract can be produced from any grape variety. In some embodiments, the grape extract is produced from a variety of red grapes. The grape extract can be obtained from any source and can be freeze dried, fresh, solid or liquid. In an embodiment, the grapes from which the grape extract is prepared are harvested and extracted in the Rhone Valley of France using only water and food-grade alcohol during the extraction process. For some embodiments, the composition contains about 0.5 to about 70 mg of grape extract.

In some embodiments, the grape extract is standardized to the amount of total polyphenolic compounds present in the grape extract. In an embodiment, the total amount of polyphenolic compounds in the grape extract ranges from about 50 to about 80 percent (w/w) of the grape extract. In an embodiment, the total amount polyphenolic compounds in the grape extract is about 75 percent (w/w) of the grape extract.

In some embodiments, the grape extract is standardized to the amount of anthocyanins present in the grape extract. In an embodiment, the total amount of anthocyanins in the grape extract ranges from about 30 to about 60 percent (w/w) of the grape extract. In an embodiment, the total amount anthocyanins in the grape extract is about 50 percent (w/w) of the grape extract.

In some embodiments, the grape extract is standardized to the amount of resveratrol present in the grape extract. In some embodiments, the amount of resveratrol present in the grape extract ranges from about 0.01 percent to about 5 percent (w/w) of the grape extract. In an embodiment, the total amount of resveratrol in the grape extract ranges from about 0.07 to about 0.16 percent (w/w) of the grape extract. In an embodiment, the total amount resveratrol in the grape extract is about 5 percent (w/w) of the grape extract.

In some embodiments, the amount of grape extract present in the final composition is based on achieving a desired amount of a compound contained within the grape extract in the final composition. In these embodiments, the amount of grape extract used is dependent upon the amount of a particular compound present in the grape extract used in the composition.

In some embodiments, the amount of polyphenolic compounds derived from the grape extract in the composition ranges from about 1 to about 5 percent (w/w) of the final composition. In an embodiment, the amount of polyphenolic compounds derived from the grape extract in the composition is about 3 percent (w/w) of the final composition.

In some embodiments, the amount of resveratrol derived from the grape extract in the composition ranges from about 0.20 to about 0.70 percent (w/w) of the final composition. In further embodiments, the amount of resveratrol derived from the grape extract in the composition ranges from about 0.29 to about 0.68 percent (w/w) of the final composition. In an embodiment, the amount of resveratrol derived from the grape extract in the composition is about 0.68 percent (w/w) of the final composition.

Formulations and Kits

Also provided herein are dietary supplement formulations containing a composition as described herein. In some embodiments, the dietary supplement formulation is administered orally in a dosage form to a subject. In some embodiments, the oral dosage form is configured to be swallowed, chewed, or dissolved in the oral cavity of a subject. The oral dosage form can be a tablet, capsule, soft gel, gel cap, liquid, paste, spray, or powder. In some embodiments, the composition is impregnated in or coated on a dissolvable sheet made of suitable non-toxic biocompatible materials. The oral dosage form can be configured for immediate release or controlled release.

In some embodiments, the dietary supplement formulation contains a pharmaceutically acceptable carrier or excipient. Suitable pharmaceutically acceptable carriers or excipients include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition. The pharmaceutical formulations can be sterilized and if desired mixed with auxiliary agents, such as lubricants, preservatives, stabilizers, wetting agents, emulsifiers, salts for influencing osmotic pressure, buffers, coloring, flavoring and/or aromatic substances and the like which do not deleteriously react with the active composition.

In some embodiments, the dosage of the dietary supplement formulation ranges from about 0.010 g to 0.015 g per kg of bodyweight. In an embodiment, the dosage of the dietary supplement formulation ranges from about 0.010 g to 0.013 g per kg of bodyweight. In another embodiment, the dosage of the dietary supplement formulation is about 0.013 g per kg of body weight.

Also provided herein are kits containing one or more composition and/or pharmaceutical formulation described herein. In some embodiments, the composition and/or pharmaceutical formulation is contained within suitable packaging within the kit. Suitable packaging includes but is not limited to, bottles, boxes, blister packages, syringes and the like. In further embodiments, the kit also includes instructions printed on or otherwise contained in a tangible medium of expression. The instructions can provide information regarding the content of the composition or pharmaceutical formulations contained therein, safety information regarding the content of the composition(s) or pharmaceutical formulation(s) contained therein, information regarding the dosages, indications for use, and/or recommended treatment regimen(s) for the composition(s) and/or pharmaceutical formulations contained therein.

Methods of Modifying Cognitive Performance

Provided herein are methods of administering the compositions and/or dietary supplement formulations described herein to a subject in need thereof. In some embodiments, the subject has normal age-related cognitive decline. In other embodiments, the subject has abnormal cognitive decline. In some embodiments, the abnormal cognitive decline is mild cognitive impairment, Parkinson's disease, Alzheimer's disease, or dementia. In some embodiments, the subject is 65 years old or older.

The composition or dietary supplement formulation is administered in a dose to a subject one or more times daily. In some embodiments, the dose is delivered in one or more dosage forms (e.g. tablets, capsules, soft gels, gel caps). In an embodiment, the dose is delivered in two capsules. In some embodiments, each dose contains about 350 mg to about 25 g of blueberry extract, about 10 mg to about 100 mg of L-carnosine, about 350 mg to about 25 g green tea extract, and about 50 IU to about 4000 IU of vitamin $D_3$. For some of these embodiments, the dose is split about evenly between the two capsules. In further embodiments, the dose also contains a pharmaceutically acceptable carrier. In one embodiment, administration of the dose occurs once daily. In some embodiments, the dose is administered in the morning. In some embodiments, the dose is administered with food. Daily administration can occur for any amount of time. In some embodiments, daily administration occurs for 1 day to one year. In other embodiments, daily administration occurs for 1 day to about 6 months. In further embodiments, daily administration occurs for 1 day to about 2 months In an embodiment, two capsules containing a composition or pharmaceutical formulation, as described herein is administered to a subject in need thereof once a day for about 2 months. In another embodiment, two capsules containing a composition or pharmaceutical formulation, as described herein, is administered to a subject in need thereof twice a day for about 2 months. In other embodiments, one capsule containing a composition or pharmaceutical formulation, as described herein, is administered to a subject in need thereof once a day for about 2 months. In other embodiments, one capsule containing a composition or pharmaceutical formulation, as described herein, is administered to a subject in need thereof once a day for about 2 months.

In some embodiments, administration of the composition or pharmaceutical formulation as described herein results in improved cognitive performance as measured by a suitable cognitive test in a subject suffering from normal age-related cognitive decline or abnormal disease or disorder, such as mild cognitive impairment, Parkinson's disease, Alzheimer's disease, or dementia as measured by a suitable cognitive test. In other embodiments, administration of the composition or pharmaceutical formulation as described herein results in a reduction in the rate of decline in cognitive performance that is due to normal aging process or an abnormal disease or disorder, such as mild cognitive impairment, Parkinson's disease, Alzheimer's disease, or dementia as measured by a suitable cognitive test. In further embodiments, administration of the composition or pharmaceutical formulation prevents or delays the onset of normal age-related cognitive decline as measured by a suitable cognitive test.

Suitable cognitive tests include, but are not limited to tests which assess episodic memory, processing speed, verbal ability, working memory, executive function, and complex speed. In some instances, episodic memory is assessed using the Auditory Verbal Learning Test (see e.g. Lezak et al., 2004. Neuropsychol. Assess. $4^{th}$ ed. Oxford University Press, New York.), which involves reading and remembering a list of 15 common English nouns. In some instances, verbal ability is assessed based upon a recognition vocabulary test (see e.g. Ekstrom et al., 1976. Educational Testing Service, Princeton, N.J.), in which the subject has to identify a synonym of a target word from one of five options. In some instances, processing speed is assessed using one or more of the following tests: the Identical Pictures Test (see e.g., Id.), the Number Comparison Task, (see e.g., Id.) and Trail Making A (see e.g., Reitan, R. et al. 1985. Neropsychol. Press. Tucson, Ariz.). In other instances, working memory is assessed using the Forward and Backward Digit Span Task (see e.g., Weschsler, D. 1981. WAIS-R manual: Weschler adult intelligence scale-revised Psychological Corp.). In further instances, executive functioning, which includes skills that are involved in the planning and execution of cognitive tasks, is assessed with Trail Making B (see e.g., Reitan, R. et al. 1985. Neropsychol. Press. Tucson, Ariz.), Category Fluency (see e.g., Benton A. L., et al. 1989. Manual of instructions. AJA, Iowa City), and Controlled Oral Word Association (see e.g., Spreen et al., 1998. A Compendium of Neruopsychological Tests: Administration, Norms, and Commentary. Oxford University Press, USA). In further instances, complex speed, which assesses the ability to do multiple mental tasks quickly using the number of correct items from the Digit Symbol test (see e.g., Weschsler, D. 1981. WAIS-R manual: Weschler adult intelligence scale-revised Psychological Corp.).

It should be understood that numerous changes may be made therein without departing from the scope of the disclosed embodiments. On the contrary, it should be clearly understood that resort may be had to various other embodiments, modifications, and equivalents thereof, which, after reading the description herein, may suggest themselves to those skilled in the art without departing from the spirit of the present embodiments and/or the scope of the appended claims. All patents, patent applications, and publications referenced herein are incorporated by reference in their entirety for all purposes.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Administration of a Formulation Containing Blueberry Extract, L-Carnosine, Green Tea Extract, Vitamin $D_3$, and Grape Extract Improves Cognitive Performance in Humans Introduction A study was initiated in humans observing the effect of administering a dietary supplement containing blueberry extract, L-carnosine, green tea extract, Vitamin $D_3$ and a full spectrum grape extract. The formulation was based on a composition described in U.S. Pat. Nos. 7,442,394 and 8,574,640. However, the formulation contained blueberry extract, L-carnosine, green tea extract, vitamin $D_3$, and a full spectrum grape extract. Briefly, the composition or placebo was administered to older adults in the form of two capsules daily for 2 months. Cognitive performance was evaluated before administration of the formulation and after two months of administrations.

Methods

Participants.

Participants were recruited from the community using advertisements in local newspapers, booths at health fairs and memory screening events, as well as by postcards using commercially available mailing lists. Inclusion criteria for the study included participants between the ages of 65-85 years who were native English speaking, able to understand and sign the informed consent, and having no evidence of dementia (Mini-Mental State Examination [MMSE] scores ≥24). Exclusion criteria for the study were history of known allergy to components of the compositions used in the study, use of high does anti-oxidant supplements other than what is provided in the study, and depressed mood as assessed by the Center for Epidemiologic Studies-Depression scale (scores greater than 5).

Measures.

In addition to the measures of cognitive performance described below, participants completed several descriptive instruments at the screening assessment. These included a questionnaire on basic demographic information, allergies, and personal medical history. Global cognitive performance was assessed using the MMSE cognitive screening tool. Self-reported health status was evaluated using the SF-12 Health Survey. Finally, depressive symptoms were assessed using the 10-item Centers for Epidemiologic Studies Depression Scale (CES-D).

Cognitive Measures.

The battery of cognitive tests included standard measures that were classified into six broad areas-episodic memory, processing speed, verbal ability, working memory, executive functioning, and complex speed. Episodic memory, or the ability to learn and remember a series of items, was measured using the Auditory Verbal Learning Test (AVLT), which involves reading and remembering a list of 15 common English nouns. Two outcomes were examined here-immediate recall (average number of words recalled across five learning trials) and delayed recall (number of words recalled after a 20-minute delay). Verbal ability was the total number correct on a recognition vocabulary test in which participants had to identify a synonym of a target word from one of five options. Processing speed provides an index of how rapidly a person can respond and was measured using the Identical Pictures Test, the Number Comparison task, and Trail Making A. For Trail Making A, an inverse transformation was applied to scores before standardization to account for this measure recording latency, rather than the number correct. Working memory provides an index of the ability to maintain some information and was measured with the Forward and Backward Digit Span task. Executive functioning includes skills that are involved in the planning and execution of cognitive tasks and was measured with Trail Making B, Category Fluency, and Controlled Oral Word Association. For Trial Making B, an inverse transformation was applied in the same manner as Trail Making A. Finally, we assessed complex speed, which assesses the ability to do multiple mental tasks quickly using the number of correct items from the Digit Symbol Test.

Interventional Compound and Randomization Schedule.

The study was double blinded. Participants were randomly assigned to receive the test composition that contains 900 mg of blueberry extract, L-carnosine, green tea extract, about 200 IU of vitamin $D_3$, and about 40 mg of a full spectrum grape extract or a matched placebo control. Participants took one pill (capsule) in the morning and one pill in the evening. Participants were encouraged to take the pills with food. Use of the composition and the placebo was covered by an Investigational New Drug Application (IND 104287) from the Food and Drug Administration and the protocol was registered with clinical trials.gov (NCT01963767). For the randomization, the schedule was stratified on the basis of age (65-74 years and 75-85 years) and participants were randomized in blocks of ten.

Procedure.

All procedures in the study were approved by the Western Institutional Review Board (IRB), and all persons who participated in the in-person assessments completed an informed consent. The first contact for potential participants was a telephone screen where basic inclusion and exclusion criteria were assessed (e.g., aged 65-85 years). An in-person screening visit was then scheduled within the next two weeks during which the MMSE, CES-D and SF-12 questionnaires were assessed. Persons who passed the screening were scheduled for a baseline visit during which participants were randomized to receive the test composition or a placebo, the cognitive measures were administered, and participants received a blood draw for safety markers (i.e., complete blood chemistry, comprehensive metabolic panel). In addition, participants received a 1-month supply of the test composition or the placebo together with a pill diary to record when the pills were taken and any adverse events that occurred.

Figure 1:
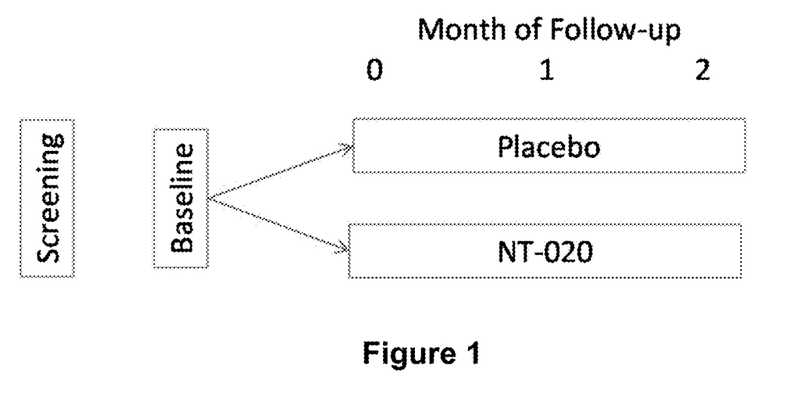
FIG. 1 shows a schedule for administration of a test composition and sequence of data collection.

One month after the start of the test administration regimen, participants returned any unused test pills or placebo along with the pill diary, received a blood draw, and received a new month's supply of the test composition or placebo. One month later, participants returned to repeat the cognitive assessment battery and return any unused test pills or placebos, along with the pill diary. In addition to the scheduled assessments described above, participants were called 1 and 3 weeks after the baseline and 1-month assessment adverse events and compliance with the test composition or placebo. FIG. 1 shows the general experimental timeline including test and control groups and data collection time points.

Statistical Analysis.

Considerations of sample size were based upon statistical power analysis. Specifically, the study was originally powered to detect a medium-sized effect (d=0.5) with a total sample size of 50 per group. The cognitive outcome analyses were conducted using analysis of co-variance (ANCOVA) values whereby scores from the final assessment point were used as the outcomes and baseline scores were co-varied. For randomized experiments with pre-test (baseline) and post-test (follow-up) measurements, usually ANCOVA should be preferred with pre-test score as a co-variant. The reason for preferring ANCOVA over repeated-measures ANOVA is that the latter has lower power and some assumptions (most prominently homogeneity of variances) that are unlikely to be met/Group status (test composition, placebo) were the between-subjects variable. A one-tailed p value of 0.05 was used for the analyses.

Results

Sample Characteristics.

Figure 2:
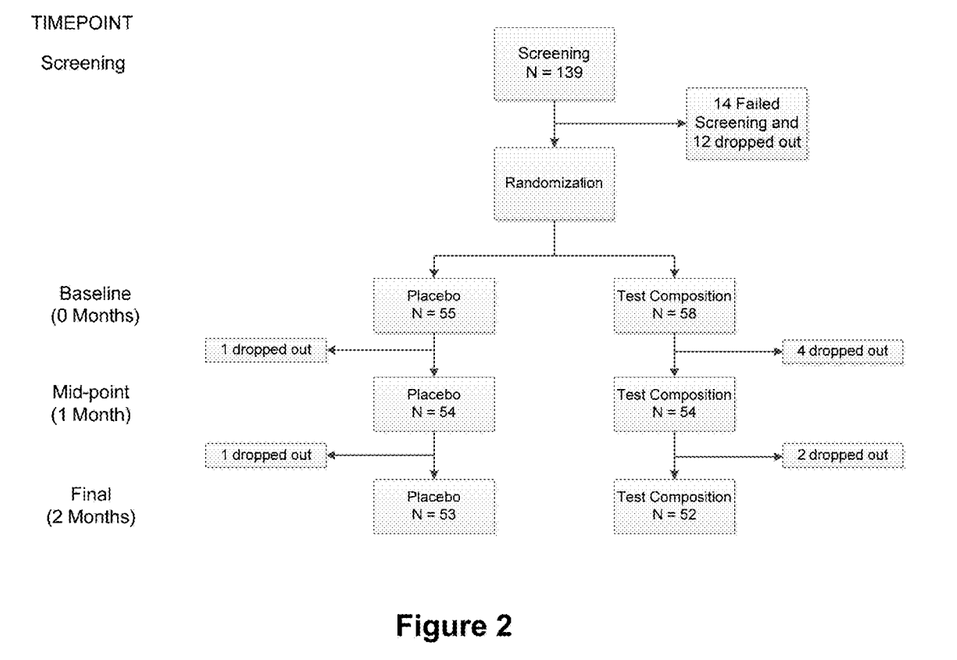
FIG. 2 shows a breakdown of a sample population used in a study to determine the effect of a test composition on cognitive performance.

FIG. 2 displays the breakdown of the sample across the longitudinal follow-up period. Of the 139 who participated in the in-person screening session, 113 (81%) were randomized to the test composition or placebo groups. Across the 2-month follow-up period, 2 persons dropped out of the placebo group and 6 dropped from the test composition group. The majority of persons who left the study indicated that they no longer had time to participate. Calculation of the difference in attrition between the groups using a Fischer exact test revealed no significant differences (p=0.273). The demographic characteristics of the sample that completed the 2 month follow-up are shown in Table 1. The sample was approximately 73 years of age, almost two-thirds were women, the majority of the sample was white, and the average MMSE score was over 29. A comparison of the two groups' t-tests or chi-squared tests revealed no statistically significant group differences.

TABLE 1

Demographic Characteristics of the Sample

| | | Placebo (n = 53) | Test Composition (n = 52) |
|---|---|---|---|
| Years of age | Mean | 74.34 | 72.82 |
| | Standard Dev. | 5.48 | 5.54 |
| Gender | % Female | 60.4 | 63.5 |
| Race/Ethnicity | % White | 100 | 92.3 |
| Years of Education | Mean | 15.61 | 15.88 |
| | Standard Dev. | 2.93 | 2.41 |
| MMSE | Mean | 29.21 | 29.37 |
| | Standard Dev. | 1.03 | 1.07 |
| CES-D | Mean | 2.75 | 2.85 |
| | Standard Dev. | 1.31 | 1.13 |
| SF-12 | Mean | 29.89 | 29.38 |
| | Standard Dev. | 2.36 | 3.09 |

Cognitive Performance.

Table 2 displays the means and the standard errors for each of the cognitive outcomes at baseline and follow-up. The results of the ANCOVA indicated that group status was statistically significant for Identical Pictures (F [1, 103]= 3.55, p=0.03; d=0.37) and there was a trend toward significance for Number Comparison (F [1, 103]=2.43, p=0.06; d=0.31). In both cases, the test composition group exhibited better performance than the placebo group. None of the other group effects were close to statistical significance (p values >0.10).

TABLE 2

Cognitive Test Scores (Mean ± SE) from Baseline and Follow-up for Placebo and Test Composition Groups

| Measure | Placebo (n = 53) | | Test Composition (n = 52) | |
| --- | --- | --- | --- | --- |
| | Baseline | Follow-up | Baseline | Follow-up |
| Identical Pictures | 21.15 ± 0.68 | 21.72 ± 0.61 | 23.06 ± 0.68 | 24.12 ± 0.65 |
| Number Comparison | 21.85 ± 0.63 | 21.60 ± 0.65 | 21.35 ± 0.64 | 21.99 ± 0.65 |
| Trailmaking A | 40.91 ± 1.52 | 39.09 ± 1.70 | 37.58 ± 1.54 | 35.11 ± 1.72 |
| Trailmaking B | 92.98 ± 6.05 | 84.60 ± 4.95 | 84.80 ± 6.16 | 78.71 ± 5.04 |
| Digit Span Forward | 10.39 ± 0.29 | 10.55 ± 0.31 | 10.69 ± 0.29 | 10.57 ± 0.31 |
| Digit Span Backward | 6.39 ± 0.33 | 7.11 ± 0.34 | 7.82 ± 0.34 | 7.73 ± 0.34 |
| Category Fluency | 15.39 ± 0.64 | 16.13 ± 0.61 | 17.21 ± 0.65 | 16.61 ± 0.62 |
| COWA | 38.98 ± 1.64 | 41.07 ± 1.49 | 40.84 ± 1.66 | 41.74 ± 1.51 |
| Vocabulary | 38.00 ± 0.97 | 38.64 ± 1.02 | 40.44 ± 0.97 | 40.71 ± 1.02 |
| AVLT-Immediate | 8.67 ± 0.27 | 9.10 ± 0.29 | 8.70 ± 0.27 | 9.23 ± 0.29 |
| AVLT-Delayed | 8.51 ± 0.44 | 8.73 ± 0.48 | 8.13 ± 0.44 | 8.98 ± 0.49 |

SE (standard error), COWA (Controlled Oral Word Association Test), AVLT (Auditory Verbal Learning Test)

Figure 3:
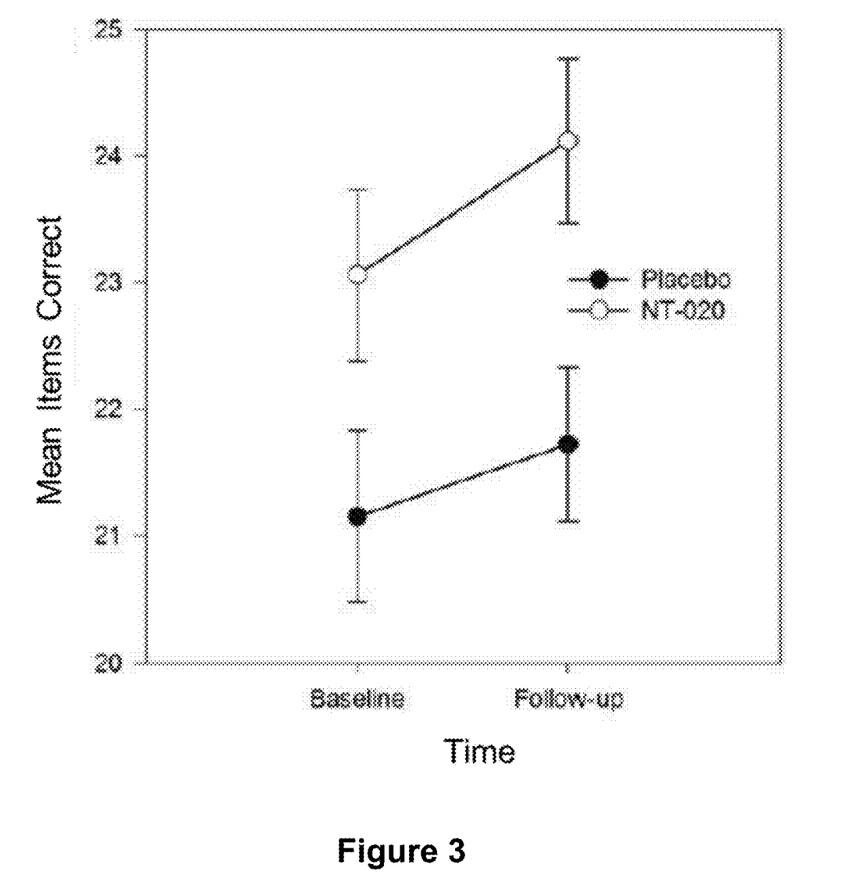
FIG. 3 shows the results from an Ideal Picture assessment in subjects receiving 2 months of treatment with a test composition or a placebo.
Figure 4:
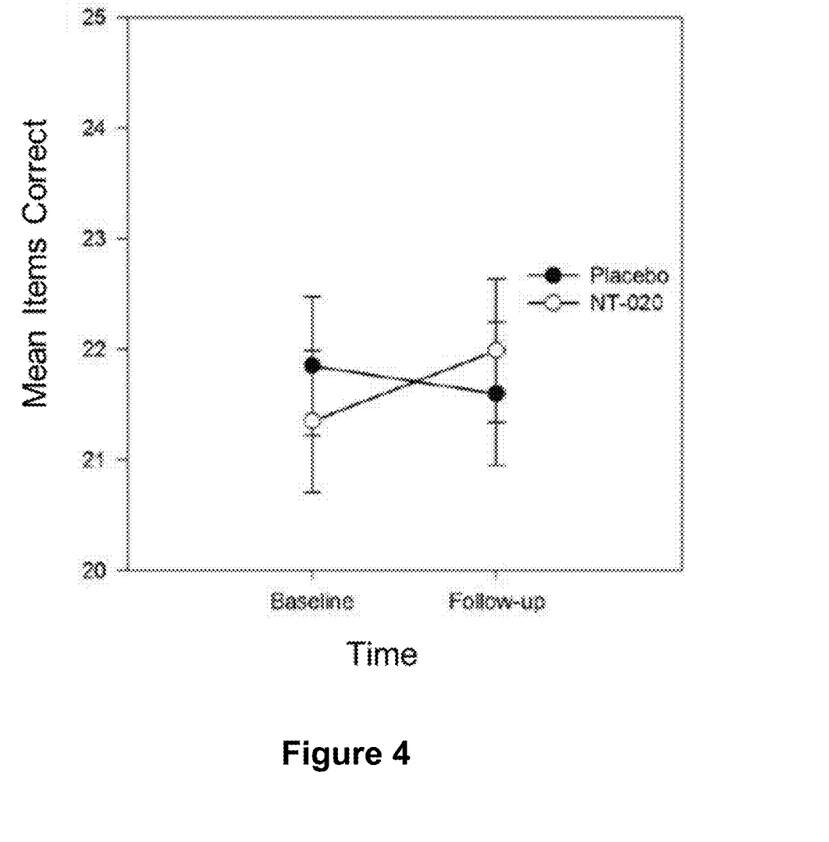
FIG. 4 shows the results from a number completion assessment in subjects receiving 2 months of treatment with a test compound or a placebo.

To better understand the effects on Identical Pictures and Number comparison, values were plotted and within-group paired t-tests on the scores from baseline and follow-up were computed. Results for Identical pictures are shown in FIG. 3. Results for Number comparison are shown in FIG. 4. For Identical Pictures, the test composition group exhibited statistically significant increases in performance (t [51]= 2.38, p=0.021), whereas the placebo group remained stable (t [52]=−1.27, p=0.211). Similarly, the test composition group exhibited significant gains across the follow-up period on Number comparison (t [51]=−2.62, p=0.012), whereas the placebo group experienced slight, but not statistically significant, declines (t [52]=0.51, p=0.611).

Compliance and adverse events. Participants completed pill and symptom diaries across the course of the follow-up period. Between the baseline and the mid-point assessment, participants averaged 1.93 doses per day out of a maximum of 2. This did not vary as a function of group ($M_{placebo}$=1.93, $M_{test\ composition}$=1.92; F [1,103]=0.06, p=0.799). Between the mid-point and the final measurement point, participants averaged 1.91 doses per day out of a maximum of 2 and this did not vary as a function of group ($M_{placebo}$=1.91, $M_{test\ composition}$=1.90; F [1,103]=0.24, p=0.625). The most commonly reported reasons for why participants missed a dose were that they forgot or had an unrelated health issue (e.g., could, fever) and decided not to take a dose that day.

Between baseline and the 1-month assessment point participants reported an average of four adverse events per person across the follow-up period, but this did not differ between intervention groups ($M_{placebo}$=4.38, $M_{test\ composition}$=4.59; F [1,103]=0.03, p=0.866). Similarly, the groups did not differ in the number of adverse events between the 1-month and 2-month follow-up points ($M_{placebo}$=1.64, $M_{test\ composition}$=1.86; F [1,103]=0.30, p=0.584). The commonly reported symptoms were changes in activity (e.g., lethargy, nervousness) or gastrointestinal symptoms (e.g., upset stomach, diarrhea). One participant exhibited a significant cardiac adverse event during the course of the study during her first month of participation. This event was reported to Western IRB and it was determined to be unrelated to her participation in the study. The study was unblinded for this participant and she was found to be in the test composition arm of the study. This participant was removed from the study.

Conclusion

The results of the study indicated improvements in at least two measures of processing speed after 2 months of daily administration of the test composition, as compared to persons on the placebo, who did not show this improvement. As such, the results suggest that cognitive performance can be improved by a pill based composition containing blueberry extract, L-carnosine, green tea extract, Vitamin $D_3$, and a full spectrum grape extract. The results are noteworthy and unexpected in that the domain of processing speed that was improved by administration of the test composition is most often affected early on in the course of normal cognitive aging and successful performance on these tasks often underlies more complex cognitive outcomes, such as memory and verbal ability. Further, administration time was relatively short (only 2 months), which is shorter than other studies. Here, improvements in processing speed, which is a domain that typically exhibits significant changes with advancing age was observed. Among persons who are cognitively intact, the domain of processing speed may be the one that is the most malleable on account of the normative declines that appear. The results further suggest that the test composition is well tolerated by older adult participants. In short, the study demonstrates improvements in one domain of cognitive performance among older adults.

We claim:

1. A method of treating cognitive decline in a subject in need thereof comprising:
   administering to said subject a dosage form of a composition, the dosage form comprising about 350 mg to about 25 g of blueberry extract; about 10 mg to about 200 mg of L-carnosine; about 350 mg to about 25 g of a green tea extract; about 50 IU to about 4000 IU of vitamin D3; and about 1 mg to about 60 mg of a grape extract.

2. The method of claim 1, wherein the grape extract is a full spectrum grape extract.

3. The method of claim 1, wherein the composition further comprises a pharmaceutically acceptable carrier or excipient.

4. The method of claim 1, wherein the administering occurs once daily.

5. The method of claim 1, wherein the administering occurs twice daily.

6. The method of claim 1, wherein the dosage form is selected from the group consisting of a tablet, capsule, soft gel, gel cap, liquid, paste, spray, or powder.

7. The method of claim 1, wherein the composition is orally administered.

8. The method of claim 1, wherein the subject has normal age-related cognitive decline.

9. The method of claim 1, wherein the administered composition improves cognitive performance as measured by a cognitive performance assessment test.

10. The method of claim 1, where the administering occurs daily for about 2 days to about 1 year.

* * * * *

UNITED STATES PATENT AND TRADEMARK OFFICE
CERTIFICATE OF CORRECTION

PATENT NO. : 9,827,285 B1
APPLICATION NO. : 14/291773
DATED : November 28, 2017
INVENTOR(S) : Bickford et al.

Page 1 of 1

It is certified that error appears in the above-identified patent and that said Letters Patent is hereby corrected as shown below:

On the Title Page

Column 1 items (71) Applicants and (72) Inventors Line 6-11:
Applicant's name Paul D. Sanberg corrected to Paul R. Sanberg.

Signed and Sealed this
Twenty-second Day of May, 2018

Andrei Iancu
*Director of the United States Patent and Trademark Office*